United States Patent [19]
Markowitz

[11] 4,411,271
[45] Oct. 25, 1983

[54] BODY TISSUE DEPOLARIZATION EVALUATION SYSTEM

[75] Inventor: H. Toby Markowitz, Anoka, Minn.

[73] Assignee: Medtronic, Inc., Minneapolis, Minn.

[21] Appl. No.: 347,522

[22] Filed: Feb. 10, 1982

[51] Int. Cl.³ .............................................. A616 5/04
[52] U.S. Cl. ................................... 128/703; 128/704
[58] Field of Search ............................... 128/702–704, 128/706, 708, 696

[56] References Cited

U.S. PATENT DOCUMENTS

| | | | |
|---|---|---|---|
| 3,209,251 | 9/1965 | Edgington et al. | 128/706 |
| 3,498,287 | 3/1970 | Erh | 128/731 |
| 3,518,983 | 7/1970 | Jorgensen | 128/702 |
| 3,554,187 | 1/1971 | Glassner et al. | 128/706 |
| 3,606,882 | 9/1971 | Abe et al. | 128/704 |
| 4,112,930 | 9/1978 | Feldman et al. | 128/704 |

FOREIGN PATENT DOCUMENTS

WO81/1659 6/1981 PCT Int'l Appl. ................ 128/702

*Primary Examiner*—Wm. E. Kamm
*Assistant Examiner*—Mitchell J. Shein
*Attorney, Agent, or Firm*—Everett J. Schroeder; Kenneth D. Siegfried; Robert O. Vidas

[57] ABSTRACT

An evaluation system for use in conjunction with a body implantable body stimulator, the body stimulator including a stimulation delivering and depolarization sensing lead system. An input connects a digitizer to the lead system, the digitizer digitizing depolarization signals sensed by the lead system. A computing system identifies excursions in the digitized depolarization signals and evaluates identified excursions in accordance with preselected merit criteria. An output gives an indication of at least that excursion having the highest merit that satisfies said merit criteria.

15 Claims, 3 Drawing Figures

BODY TISSUE DEPOLARIZATION EVALUATION SYSTEM

DESCRIPTION

BACKGROUND OF PRIOR ART

Physiological waveform processors are known to the prior art for such purposes as detecting the occurrence of a particular waveform characteristic. For example, such devices have been used to detect the occurrence of an R-wave or a QRS complex within an ECG.

Typical prior art devices of the type described recognize that the slope or slew rate of the waveform characteristic of interest often differs from that of the remainder of the waveform. When the characteristic of interest has a greater slew rate than other waveform characteristics, a mere comparison of the derivative of the waveform signal against a reference value can reliably detect the occurrence of the characteristic of interest. In an environment where noise or other extraneous signals are likely to be present, a second criterion may be employed to reduce the probability of a false indication of the waveform characteristic of interest.

A prior art device which employs the slope or slew rate of a waveform to detect the occurrence of a particular waveform characteristic is shown in U.S. Pat. No. 3,878,833, issued Apr. 22, 1975, for Physiological Waveform Detector. The referenced patent includes an embodiment which detects the occurrence of the QRS complex in the ECG waveform essentially by comparing the derivative of the waveform signal with a reference signal and determining whether the derivative signal exceeds the reference signal for a predetermined period of time. Thus, two criteria are employed to detect the QRS complex: namely, magnitude and duration. The magnitude criterion distinguishes between the QRS complex and other portions of the ECG as well as low frequency artifacts and noise. The duration criterion distinguishes between the QRS complex and muscle spikes, pacemaker pulses and other high frequency artifacts.

Prior art devices of the type disclosed in the referenced patent can detect a QRS complex in an ECG and other waveform characteristics within other waveforms. The process of detection by comparison with a reference value, however, merely gives an indication of the occurrence of the characteristic of interest without any indication as to the parameters of that characteristic. Further, the criteria employed by this prior art device may not be the most reliable or desirable to establish the occurrence of the characteristic. For example, in determining whether or not a cardiac pacing lead is properly placed, peak-to-peak amplitude and slew rate may be far more valuable than the magnitude and duration of a waveform characteristic.

A signal processor which establishes peak-to-peak amplitude between a waveform signal peak and the next successive peak as well as the slew rate of the waveform signal between successive waveform signal peaks is disclosed in United States Patent Application Ser. No. 180,710, filed Aug. 25, 1980, for Physiological Waveform Processor which is co-owned with the present invention. This system determines the maximum peak-to-peak amplitude of the waveform signal and its associated slew rate. The occurrence of a particular waveform characteristic is detected by comparing the maximum peak-to-peak amplitude and its associated slew rate against reference values. If the reference values are satisfied, the system may then indicate that the waveform characteristic has, in fact, occurred. For example, comparison of the maximum peak-to-peak amplitude, and its associated slew rate, against reference values may be employed to detect the occurrence of a QRS complex in an ECG waveform, as in a sense amplifier or cardiac pacemaker, or to check the lead placement for a cardiac pacemaker. However, this system requires that that portion of the waveform being processed that has the maximum peak-to-peak amplitude also has the greatest merit or probability that it is the characteristic of interest. In fact, a noise spike may have a higher peak-to-peak amplitude than other portions of the waveform being processed. Such a noise spike would not likely be detected as a QRS complex as a result of filtering and the slew rate comparison. However, if detected, it could prevent a detection of the QRS complex as a result of its higher peak-to-peak amplitude. Thus, this latter mentioned system can reliably give an indication that it has detected as QRS complex but may not always reliably detect that complex. Further, it is limited to a detection of those complexes having the highest peak-to-peak amplitude in the waveform.

BRIEF SUMMARY OF INVENTION

The present invention provides an evaluation system for waveforms of physiological origin. The waveform is evaluated by identifying excursions in the waveform signal (that portion of the signal between waveform peaks) and evaluating identified excursions in accordance with a preselected plurality of merit criteria. If those criteria include peak-to-peak amplitude and slew rate, for example, an excursion may have a higher merit even though it has a lower peak-to-peak amplitude. Thus, a noise spike having the highest peak-to-peak amplitude within the waveform being evaluated can be rejected as not satisfying the merit criteria because of inadequate duration while the evaluation system does evaluate a waveform characteristic or excursion of lower peak-to-peak amplitude as satisfying the merit criteria. Accordingly, the certainty of detection of the desired characteristic is enhanced over the prior art systems described above. Also, the system of the present invention is more versatile than prior art systems in that it does not depend on identifying a maximum in one of its merit criteria.

In a preferred embodiment, the system of the present invention is implemented in conjunction with a body implantable stimulator of the type having a stimulation delivering and depolarization sensing lead system. The evaluation system may form a part of the stimulator, as the sense amplifier of a cardiac pacemaker, or, alternatively, may be employed to check lead placement for the purpose of threshold evaluation and/or compatibility of the lead placement with the sensitivity of the stimulator. An input connects the lead system to a digitizer which digitizes depolarization signals sensed by the lead system. A computing system identifies excursions in the digitized depolarization signals and evaluates identified excursions in accordance with a preselected plurality of merit criteria. An output is connected to the computing system for giving an indication of at least that excursion having the highest merit that satisfies the merit criteria. For the purpose of this specification and claims, the term "excursion" is intended to embrace that portion of a waveform lying between two changes in slope of the waveform and further includes "notched" and "tailing" portions of the waveform, as defined below. The term "merit" embraces the relative reliability of the parameters of a particular waveform characteristic or excursion as establishing that a particular characteristic or excursion is that characteristic it is desired to detect. For example, an excursion of higher merit is a more reliable indication of the occurrence of a particular characteristic than is an excursion of lower merit. Among the merit criteria that may be employed in evaluating identified excursions are excursion slew rate, excursion peak-to-peak amplitude, excursion duration and, for excursion subsequent to a first excursion satisfying the merit criteria, the relative peak-to-peak amplitude and the time of occurrence following the first evaluated excursion that satisfies the merit criteria.

DETAILED DESCRIPTION OF DRAWINGS

Figure 1:
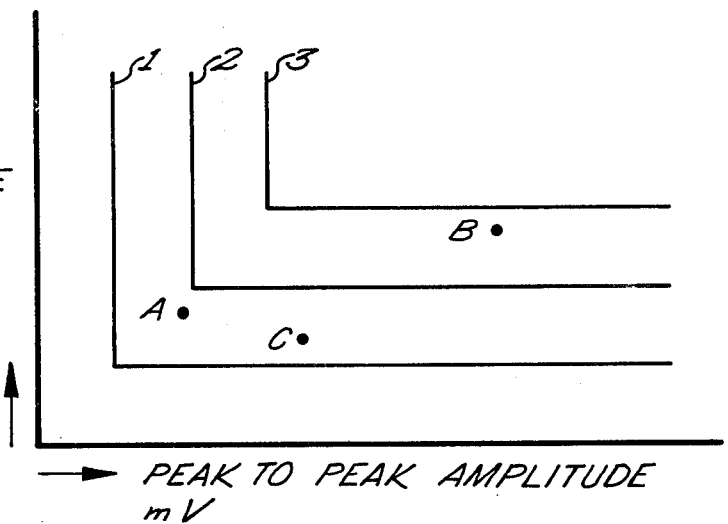
FIG. 1 is a graph that illustrates the merit concept underlying the present invention.

Referring now to FIG. 1, there is shown a graph that illustrates the merit concept of the present invention. FIG. 1 is a plane Cartesian coordinate system having peak-to-peak amplitude as the abcissa and slew rate as the ordinate. The waveform characteristic to which the graph of FIG. 1 is directed is the QRS complex.

FIG. 1 defines a region above it and to its right that has higher merit in the detection of the QRS complex than the region to its left and below it. That is, an excursion whose parameters fall within the region above and to the right of line 1 is a more reliable indicator that that excursion is, or is a part of, the QRS complex than an excursion whose parameters fall below or to the left of the line 1. Line 2 similarly defines a region of merit, that region having a higher merit than the region defined by the line 1 while the line 3 defines a region of yet higher merit. As described to this point, the points labeled A and C in FIG. 1 fall within the same merit region while the Point B falls within a higher merit region. Of course, other merit criteria beyond slew rate and peak-to-peak amplitude may be employed to evaluate a particular excursion.

Figure 2:
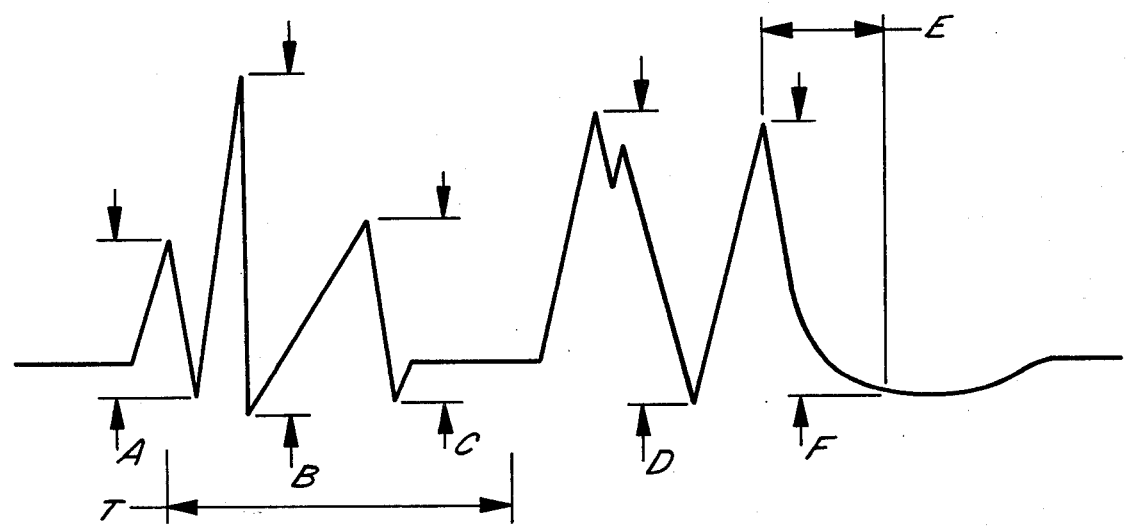
FIG. 2 shows a waveform that illustrates the application of the merit system shown graphically in FIG. 1.

With reference to FIG. 2, there is shown a waveform in which the amplitude of the first three negative excursions is indicated by the Arrows A, B and C. These three excursions represent the Points A, B and C in FIG. 1. That is, the first negative excursion (A) has a higher slew rate and lower amplitude than the third negative excursion (C) while the second negative excursion (B) has both a higher slew rate and peak-to-peak amplitude than either of the other two negative excursions of the waveform discussed to this point. As noted above, applying the merit criteria of slew rate and peak-to-peak amplitude results in the negative excursion whose amplitude is indicated at B having a higher merit. The remaining portion of the waveform illustrated in FIG. 2 is discussed below.

The above discussion focuses on the down slope or negative sloped portion of a waveform as an excursion. However, an excursion can be defined to be the up slope of a waveform, the down slope of a waveform, or both. A single slope implementation is here preferred for ease of implementation with the down slope being the most prominent single slope in the majority of QRS complexes and, thus, the slope of choice. However, the term "excursion" is intended to embrace an up slope excursion, a down slope excursion, and a double slope excursion as well as excursions having notches and trailing excursions, as discussed below.

In addition to slew rate and peak-to-peak amplitude, other merit criteria may be employed in evaluating an excursion. Among these are excursion duration which will generally fall within a range having lower and upper limits which are expected of the characteristic of interest, the QRS complex, for example. Other merit criteria that may be employed include relative amplitude and timing of an excursion relative to a first excursion that satisfies the merit criteria. For example, within the context of heart depolarizations, a subsequent excursion of greater peak-to-peak amplitude that satisfies the same merit criteria as an earlier excursion and which occurs within a preselected period of time following the first excursion is determined to have a higher merit (that is a better reliability as an indicator of the QRS complex). In this context, desirable merit criteria are an excursion slew rate greater than 0.1 volts per second, an excursion peak-to-peak amplitude greater than 1.0 millivolts, an excursion duration greater than 3 milliseconds but no greater than 30 milliseconds and, for subsequent excursions following a first excursion that satisfies these merit criteria, a greater relative peak-to-peak amplitude and the occurrence of the subsequent excursion within a preselected interval, 200 milliseconds, for example. Thus, assuming excursions having the amplitudes indicated at A, B and C in FIG. 2, and that each satisfy at least the merit criteria of Region 1 of FIG. 1, Excursion A would be evaluated as satisfying these criteria as would Excursion B. Indeed, Excursion B would be evaluated as the excursion of highest merit under either the criteria of Region 1 set out above or the higher merit criteria of Region 2. However, Excursion C would not satisfy the Region 1 criteria because it is a subsequent excursion not greater in peak-to-peak amplitude than the last occurring excursion that satisfied those criteria. Also, If either Excursion B or C occurred after the preselected interval following Excursion A, those excursions would not satisfy the merit criteria.

Figure 3:
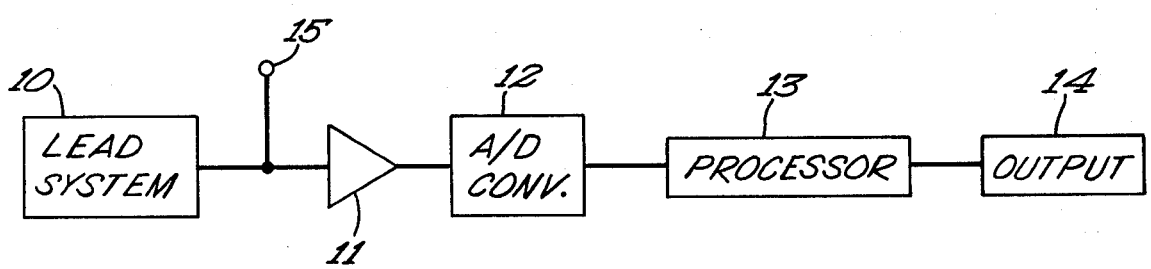
FIG. 3 illustrates, the block diagram form, an implementation of the present invention.

FIG. 3 illustrates a block diagram of a preferred implementation of the present invention. A lead system 10 which forms a part of a body implantable body stimulator includes a stimulation delivering and depolarization sensing lead system. Depolarization signals sensed by the lead system are amplified by an amplifier 11 and applied as an analog input to an analog to digital converter 12. The digitized depolarization signals are connected as an input to a processor which includes a computing system for identifying excursions in the digitized depolarization signals and for evaluating identified excursions in accordance with a preselected plurality of the merit criteria discussed above. The processor 13 is connected to an output 14, the output 14 giving an indication of at least that excursion having the highest merit that satisfies the merit criteria. In a preferred embodiment, the output gives an indication of the first evaluated excursion satisfying the merit criteria and excursions evaluated subsequent to the first indicated excursion having greater merit than the last indicated excursion. The output may be in the form of a display to display the peak-to-peak amplitude of indicated excursions. In this instance, the display may be employed to check the placement of the lead system 10 or to evaluate the probable response of a body stimulator to be connected to the lead system. In this instance, connection of a body stimulator to the lead system may be at the terminal 15. Preferably, the display will be digital or an analog printing with the excursion of highest merit identified. Alternatively, elements 11-14 of FIG. 3 may be employed as a sense amplifier of a cardiac pacemaker to identify the occurrence of a QRS complex in an ECG waveform.

Implementation of the preferred embodiment illustrated in FIG. 3 may be by any suitable components. For example, in an external system for evaluation of lead placement and pacemaker response, a National Semiconductor ADC0808 analog digital converter may be employed for element 12 while a NCS 800 microprocessor may be employed to implement the processor 13. With these components, a program listing that may be employed to implement the present invention in the manner described above is attached hereto as Table I. However, other programming may be employed without departing from the scope of the present invention.

Obviously, many modifications and variations of the present invention are possible in light of the above teachings. For example, one set of merit criteria may be established the satisfaction of which is indicated by the present invention in accordance with the above discussion. Alternatively, two or more merit criteria may be established, each having differing merit. Implementations employing either of these approaches are embraced within the present invention. In addition, excursions having a notch such as that excursion having an amplitude indicated at D in FIG. 2 may be treated as a single excursion, provided the timing and other characteristics of the notch satisfy established design parameters. For example, the notch should occur within 15 milliseconds following the beginning of the down slope and be small compared to the overall excursion peak-to-peak amplitude. Additionally, down slopes that trail off as indicated by the down slope whose amplitude is indicated at F in FIG. 2 may be treated as a "routine" down slope for the purposes of the present invention taking the peak-to-peak amplitude of the down slope to be that amplitude of the down slope at a predetermined period of time following the beginning of the down slope, 30 milliseconds, for example. Further, the processor 13 may operate on a real time basis or, alternatively, may include a memory for storage of digitized depolarization signals for later processing, as desired. The program listing that may be employed to implement the present invention in the manner described above is attached hereto as Table I. However, other programming may be employed without departing from the scope of the present invention. It is therefore to be understood that, within the scope of the appended claims, the invention may be practiced otherwise than as specifically described.

TABLE I

```
ERR LINE  ADDR   B1 B2 B3 B4        SLEW RATE/PEAK-TO-PEAK
    04-AUG-81   18:01    PAGE    1

1                                TITLE    'SLEW RATE/PEAK-TO-PEAK'
      2                                NAME     SLPKPK
      3                                EXTRN    AN,ADDROK,ATMAX,AV,BN,BUFFER
      4                                EXTRN    CSRAM,DIFF,DIVIDE
      5                                EXTRN    EGMCOL,EGMSCL,EGMSIZ,ERROR
      6                                EXTRN    LASTYP,MAX,MEAS,MLTADE,MLTPLY
      7                                EXTRN    NEGHL,NOISE,NYOLD
      8                                EXTRN    _OFFSET,PKPK,PKPKX,RESULT
      9                                EXTRN    SCORE,SLEW,SLEWCT,SLEWX,STRING
     10                                EXTRN    TYPE,XLEFT,XRIGHT
     11                                PUBLIC   SLEWPT,SLEWRT,SLPKPK
     12                                LIST     R
     13                                NLIST    M
     14                        ;
     15                        ;
     16                                DSEG
     17                        ;
     18  0000                  SLEWPT: DEFS     2         ;PTR TO START OF SEGMENT
     19                        ;
     20                                CSEG
     21                        ;
     22                                INSERT   JRCMAZ.ASM
     23                        CLR     MACR
     24                                XOR      A
     25                                ENDM
     26                        ;
     27                        TEST    MACR
     28                                AND      A
     29                                ENDM
     30                        ; EOF ON JRCMAZ.ASM
     31                        ;
     32  0000  CD 00 00   E    SLPKPK: CALL     EGMCOL    ;COLLECT AN EGM BUFFER
     33  0003  CD 0B 00   C            CALL     SLEWRT    ;CALCULATE THE SLEW RATE
     34  0006                          CLR                ;TURN OFF 'STRING' SO
     36  0007  32 00 00   E            LD       (STRING),A ;  1 PARAM WILL PRINT
     37  000A  C9                      RET
     38                        ;
     39                        ; ----------------------
```

SLEW RATE/PEAK-TO-PEAK

```
ERR LINE ADDR  B1 B2 B3 B4
    04-AUG-81 18:01  PAGE  2

40                                  ; SLEW-RATE CALCULATIONS
     41                                  ; --------------------
     42  000B              SLEWRT: CLR                      ;
     44  000C  32 00 00  E         LD    (LASTYP),A         ;CLEAR PREVIOUS-TYPE
     45  000F  32 00 00  E         LD    (ADDROK),A         ; AND "IX-1"-IS-OK FLG
     46  0012  3C                  INC   A                  ;A <- 1
     47  0013  32 00 00  E         LD    (ERROR),A          ;SET ERROR FLG FOR NOW
     48  0016  ED 52                SBC  HL,HL              ;(CY=0 ALREADY) HL <- 0
     49  0018  22 00 01  E         LD    (MAX),HL           ;INITIALIZE MAXIMUM
     50  001B  2B                  DEC   HL                 ;MAKE 'UNDEFINED' CODE
     51  001C  22 00 00  E         LD    (SLEW),HL          ;SET SLEW-RATE,
     52  001F  22 00 00  E         LD    (PKPK),HL          ; PEAK-TO-PEAK,
     53  0022  22 00 00  E         LD    (SLEWPT),HL        ; LOCATION, AND
     54  0025  22 00 01  E         LD    (RESULT),HL        ; RESULT "UNDEFINED"
     55  0028  21 00 03  E         LD    HL,CSRAM
     56  002B  22 00 00  E         LD    (XRIGHT),HL        ;INIT RT-END POINTER
     57  002E  7E                  LD    A,(HL)             ;GET 1ST SAMPLE VALUE
     58  002F  CD 31 01  C         CALL  LSQNIT             ;INITIALIZE 8-SAMPL BUFR
     59  0032  21 F8 FF  E         LD    HL,-SGMSIZ-8       ;#SMPLS,STOP 8 SHORT
     60  0035  22 00 00  E         LD    (SLEWCT),HL        ;SET UP SAMPLE-COUNT
     61  0038  DD 21 00 03 E       LD    IX,CSRAM           ;POINT TO SAMPLE BUFFER
     62  003C  CD 41 02  C  SL10:  CALL  LSQFT              ;GET SLOPE THRU HERE
     63  003F                      TEST                     ;IS IT FLAT?
     65  0040  20 07               JR    NZ,SL20-$          ;NO: SL20
     66  0042  CD 65 01  C         CALL  NEXT               ;YES:SET FOR NEXT SAMPLE
     67  0045  20 F5               JR    NZ,SL10-$          ;END OF BUFFER?NO:SL10
     68  0047  18 45               JR    SL50-$             ;YES: SL50
     69  0049  3A 00 00  E  SL20:  LD    A,(LASTYP)         ;GET PREVIOUS TYPE
     70  004C                      TEST                     ;WAS IT ZERO?
     72  004D  20 1D               JR    NZ,SL30-$          ;NO: SL30
     73  004F  2A 00 00  E         LD    HL,(XRIGHT)        ;YES:GET (XRIGHT)PTR
     74  0052  EB                  EX    DE,HL              ; IN DE-PAIR
     75  0053  DD E5               PUSH  IX                 ;MOVE CURRENT POINTER
     76  0055  E1                  POP   HL                 ; INTO HL-PAIR
     77                                                     ;CARRY-FLG ALREADY CLEAR
     78  0056  ED 52               SBC   HL,DE              ;GET (CURRENT)-(XRIGHT)
     79  0058  7C                  LD    A,H                ;GET HI BYTE OF DIFFERNC
     80  0059                      TEST                     ;IS IT ZERO?
     82  005A  20 10               JR    NZ,SL30-$          ;NO: SL30
     83  005C  7D                  LD    A,L                ;YES: IS DIFFERENCE
     84  005D  FE 0B               CP    11                 ; GREATER THAN 10?
     85  005F  30 0B               JR    NC,SL30-$          ;YES: SL30
     86  0061  CD 5B 01  C         CALL  SHIFT              ;NO: XLEFT <- (XRIGHT)
     87  0064                      TEST                     ;TURN CARRY-FLAG OFF
     89  0065  26 00               LD    H,0                ;DIVIDE DIFFERENCE
     90  0067  1F                  RRA                      ; BY TWO
     91  0068  6F                  LD    L,A                ;PUT QUOTIENT IN HL-PAIR
     92  0069  19                  ADD   HL,DE              ;CREATE MIDPOINT:OLD,NEW
     93  006A  18 03               JR    SL35-$
     94  006C  CD 5B 01  C  SL30:  CALL  SHIFT              ;XLEFT<-(XRIGHT);NEW(RT)
     95  006F  CD 74 01  C  SL35:  CALL  MARKIT             ;MARK THIS POINT
     96  0072  CD 65 01  C  SL40:  CALL  NEXT               ;SET FOR NEXT SAMPLE
     97  0075  28 17               JR    Z,SL50-$           ;ANY MORE? NO: SL50
     98  0077  CD 41 02  C         CALL  LSQFT              ;YES:GET SLOPE THRU HERE
     99  007A  21 00 00  E         LD    HL,LASTYP          ;POINT TO OLD TYPE
    100  007D  BE                  CP    (HL)               ;NEW TYPE SAME AS OLD?
    101  007E  28 F2               JR    Z,SL40-$           ;YES: SL40
    102  0080  CD 5B 01  C         CALL  SHIFT              ;XLEFT<-(XRIGHT);NEW(RT)
    103  0083  CD 74 01  C         CALL  MARKIT             ;MARK THIS POINT
    104  0086  3A 00 00  E         LD    A,(TYPE)           ;WAS THIS A
    105  0089                      TEST                     ; "FLAT" SLOPE?
    107  008A  28 B0               JR    Z,SL10-$           ;YES: SL10
    108  008C  18 E4               JR    SL40-$             ;NO: SL40
    109
    110                                  ; ADJUST FINAL VALUES FOR USER'S SCALE FACTORS
    111                                  ; -----------------------------------------
    112  008E  3A 00 00  E  SL50:  LD    HL,(MAX)           ;IS MAXIMUM-SCORE
    113  0091  7C                  LD    A,H                ; STILL ZERO?
    114  0092  BE                  OR    L
    115  0093  CA 1F 01  C         JP    Z,SL97             ;YES: NO PEAKS FOUND
```

```
ERR LINE  ADDR   B1 B2 B3 B4              SLEW RATE/PEAK-TO-PEAK
    04-AUG-81   18:01   PAGE    3

116  0096   ED 5B 00 00  E            LD      DE,(SLEW)    ;NO: CHECK HIGH LIMIT
    117  009A   21 7D F9                  LD      HL,-1667     ;ASSUME SCALE FACTOR 1
    118  009D   3A 00 00     E            LD      A,(EGMSCL)   ;GET EGM SCALE FACTOR
    119  00A0   3D                        DEC     A            ;IS IT REALLY SCALE 1?
    120  00A1   28 09                     JR      Z,SL55-$     ;YES: SL55
    121  00A3   21 E5 BE                  LD      HL,-16667    ;NO: ASSUME FACTOR 2
    122  00A6   3D                        DEC     A            ;IS IT REALLY 2?
    123  00A7   28 03                     JR      Z,SL55-$     ;YES: SL55
    124  00A9   21 4D EA                  LD      HL,-5555     ;NO: WAS SCALE FACTOR 3
    125  00AC   19              SL55:     ADD     HL,DE        ;IS SLEW RATE TOO HIGH?
    126  00AD   38 70                     JR      C,SL97-$     ;YES: SL97
    127  00AF   21 05 00                  LD      HL,5         ;NO: BEGIN CONVERSION OF
    128  00B2   CD 00 00     E            CALL    DIVIDE       ; VALUES TO USER'S SCALE
    129  00B5   7D                        LD      A,L          ;CHECK REMAINDER
    130  00B6   FE 03                     CP      3            ;NEED TO ROUND UP?
    131  00B8   38 01                     JR      C,SL60-$     ;NO: SL60
    132  00BA   13                        INC     DE           ;YES: DO THAT
    133  00BB   21 3C 00        SL60:     LD      HL,60        ;ASSUME SCALE 1 AGAIN
    134  00BE   3A 00 00     E            LD      A,(EGMSCL)   ;GET SCALE FACTOR
    135  00C1   3D                        DEC     A            ;REALLY SCALE 1?
    136  00C2   28 07                     JR      Z,SL65-$     ;YES: SL65
    137  00C4   2E 06                     LD      L,6          ;NO: ASSUME FACTOR 2
    138  00C6   3D                        DEC     A            ;REALLY 2?
    139  00C7   28 02                     JR      Z,SL65-$     ;YES: SL65
    140  00C9   2E 12                     LD      L,18         ;NO: .18MV/DOT, THEN
    141  00CB   CD 00 00     E  SL65:     CALL    MLTPLY       ;TIMES [$.1MV/DOT]
    142  00CE   50                        LD      D,B          ;MOVE PRODUCT
    143  00CF   59                        LD      E,C          ; TO DE-PAIR
    144  00D0   21 32 00                  LD      HL,50        ;FINISH DIVIDING BY 250
    145  00D3   CD 00 00     E            CALL    DIVIDE       ;(/5; *SCALE; /50)
    146  00D6   7D                        LD      A,L          ;GET REMAINDER
    147  00D7   FE 19                     CP      25           ;NEED TO ROUND?
    148  00D9   38 01                     JR      C,SL70-$     ;NO: SL70
    149  00DB   13                        INC     DE           ;YES: ROUND QUOTIENT UP
    150  00DC   ED 53 00 00  E  SL70:     LD      (RESULT),DE  ;STORE SLEW RESULT
    151  00E0   11 3C 00                  LD      DE,60        ;START CONVERTING PK-PK
    152  00E3   3A 00 00     E            LD      A,(EGMSCL)   ;SAME BUSINESS AGAIN
    153  00E6   3D                        DEC     A            ; ABOUT ASSUMING A SCALE
    154  00E7   28 07                     JR      Z,SL75-$     ; AND THEN SEEING IF
    155  00E9   1E 06                     LD      E,6          ; THAT WAS RIGHT,
    156  00EB   3D                        DEC     A            ; ETC..
    157  00EC   28 02                     JR      Z,SL75-$     ; ETC.
    158  00EE   1E 12                     LD      E,18
    159  00F0   3A 00 00     E  SL75:     LD      A,(PKPK)     ;GET #DOTS PEAK-TO-PEAK
    160  00F3   CD 00 00     E            CALL    MLTADE       ;GET 100 TIMES [#MV]
    161  00F6   50                        LD      D,B          ;MOVE PRODUCT
    162  00F7   59                        LD      E,C          ; TO DE-PAIR
    163  00F8   21 0A 00                  LD      HL,10        ;GET 10 TIMES [#MV]
    164  00FB   CD 00 00     E            CALL    DIVIDE       ;(=USER'S SCALING)
    165  00FE   7D                        LD      A,L          ;GET REMAINDER
    166  00FF   FE 05                     CP      5            ;NEED TO ROUND UP?
    167  0101   38 01                     JR      C,SL80-$     ;NO: SL80
    168  0103   13                        INC     DE           ;YES: ROUND QUOTIENT UP
    169  0104   CD 22 01     C  SL80:     CALL    SL98         ;STORE ATR/VEN PEAK-PEAK
    170  0107   2A 00 00     E            LD      HL,(ATMAX)   ;GET SEGMENT LOCATION
    171  010A   11 01 00     E            LD      DE,CSRAM+1   ;CONVERT TO SAMPLES-
    172  010D                             CLR                  ; BEFORE-START-OF-ARROW
    174  010E   ED 52                     SBC     HL,DE        ;IS THE RESULT
    175  0110   38 02                     JR      C,SL90-$     ; NEGATIVE? YES: SL90
    176  0112   20 03                     JR      NZ,SL95-$    ;NO: ZERO? NO: SL95
    177  0114   21 01 00        SL90:     LD      HL,1         ;FORCE ARROW @ LEFT EDGE
    178  0117   22 00 00     D  SL95:     LD      (SLEWPT),HL  ;STORE FOR DISPLAY
    179  011A                             CLR                  ;MADE IT ALL THE WAY:
    181  011B   32 00 00     E            LD      (ERROR),A    ; CLEAR ERROR FLAG
    182  011E   C9                        RET
    183                                   ;
    184  011F   11 FF FF        SL97:     LD      DE,-1        ;GET "UNDEFINED" CODE
    185                                   ;
    186  0122   3A 00 00     E  SL98:     LD      A,(AV)       ;GET ATR/VEN FLAG
    187  0125   21 4B 00     E            LD      HL,MEAS-1+76 ;PT TO ATRIAL PK-PK
    188  0128   3D                        DEC     A            ;IS THIS REALLY ATRIAL?
```

```
ERR LINE  ADDR  B1 B2 B3 B4             SLEW RATE/PEAK-TO-PEAK
    04-AUG-81  18:01  PAGE   4

189  0129  28 02                JR      Z,SL99-$  ;YES: SL99
    190  012B  23                   INC     HL        ;NO: POINT TO
    191  012C  23                   INC     HL        ; VENTRICULAR PEAK-PEAK
    192  012D  73           SL99:   LD      (HL),E    ;STORE LOW BYTE
    193  012E  23                   INC     HL        ;POINT TO HIGH BYTE
    194  012F  72                   LD      (HL),D    ;STORE HIGH BYTE
    195  0130  C9                   RET
    196                             ;
    197                             ;*****************************************
    198                             ;* SUBROUTINE 'LSQNIT' INITIALIZES (OR, RE- *
    199                             ;* INITIALIZES) THE PARAMETERS USED BY THE *
    200                             ;* 'LSQFT' ROUTINE. UPON FIRST ENTRY OR UPON *
    201                             ;* ENCOUNTERING A STEEP SLOPE WHOSE VALUE IS *
    202                             ;* TO BE REMOVED FROM THE BUFFER.           *
    203                             ;* THE NINE BYTES AT 'BUFFER' ARE USED AS A *
    204                             ;* POINTER (WITH VALUES '1' THROUGH '8'), AND *
    205                             ;* 8 BYTES COMPRISING A CIRCULAR BUFFER.    *
    206                             ;*****************************************
    207                             ;
    208  0131  06 08        LSQNIT: LD      B,8        ;SET TO FILL 8 BYTES
    209  0133  21 00 00  E          LD      HL,BUFFER  ;PT TO CIRCULAR BUFFER
    210  0136  36 08                LD      (HL),8     ;INITIALIZE ITS OWN PTR
    211  0138  23           LN10:   INC     HL         ;POINT TO NEXT SLOT
    212  0139  77                   LD      (HL),A     ;FILL WITH 1ST-SMPL VALU
    213  013A  10 FC                DJNZ    LN10-$     ;LOOP ON 8 BYTES
    214  013C  26 00                LD      H,0        ;UPPER BYTE = 0
    215  013E  6F                   LD      L,A        ;MAKE 16-BIT EQUIVALENT
    216  013F  29                   ADD     HL,HL      ;INITIALIZE
    217  0140  29                   ADD     HL,HL      ; (AN) TO
    218  0141  29                   ADD     HL,HL      ; 8 TIMES
    219  0142  22 00 00  E          LD      (AN),HL    ; FIRST-SAMPLE VALUE
    220  0145  29                   ADD     HL,HL      ;INITIALIZE (BN) TO
    221  0146  22 00 00  E          LD      (BN),HL    ; 16 TIMES 1ST-SAMP VALU
    222  0149  6F                   LD      L,A
    223  014A  26 00                LD      H,0        ;MAKE 16-BIT EQUIVALENT
    224  014C  11 58 FE             LD      DE,-352    ;BIAS AMOUNT (SEE BELOW)
    225  014F  CD 00 00  E          CALL    MULTPLY    ;FROM INITIAL AN, BN
    226  0152  60                   LD      H,B        ;(PRODUCT IS FORMED
    227  0153  69                   LD      L,C        ; IN BC-PAIR)
    228  0154  CD 00 00  E          CALL    NEGHL      ;HL <- -352*(FIRST SMPL)
    229  0157  22 00 00  E          LD      (OFFSET),HL ;SAVE BIAS AMOUNT
    230  015A  C9                   RET
    231                             ;
    232                             ;*****************************************
    233                             ;* SUBROUTINE 'SHIFT' MOVES THE OLD (XRIGHT) *
    234                             ;* TO "XLEFT", AND GETS THE IX-POINTER IN THE *
    235                             ;* HL-PAIR FOR STORING AS THE NEW (XRIGHT).  *
    236                             ;*****************************************
    237                             ;
    238  015B  2A 00 00  E  SHIFT:  LD      HL,(XRIGHT) ;MOVE "XRIGHT"
    239  015E  22 00 00  E          LD      (XLEFT),HL  ; TO "XLEFT"
    240  0161  DD E5                PUSH    IX          ;MOVE CURRENT POINTER
    241  0163  E1                   POP     HL          ; INTO HL-PAIR
    242  0164  C9                   RET                 ;(USER STORES HL-PAIR)
    243                             ;
    244                             ;*****************************************
    245                             ;* SUBROUTINE 'NEXT' PREPARES FOR THE NEXT *
    246                             ;* SAMPLE BY INCREMENTING THE POINTER AND  *
    247                             ;* DECREMENTING THE COUNT WHILE SETTING    *
    248                             ;* FLAGS TO INDICATE WHETHER OR NOT THERE  *
    249                             ;* ACTUALLY ARE ANY MORE SAMPLES.          *
    250                             ;*****************************************
    251                             ;
    252  0165  DD 23        NEXT:   INC     IX          ;INCREMENT POINTER
    253  0167  2A 00 00  E          LD      HL,(SLEWCT) ;GET SAMPLES-LEFT CT
    254  016A  2B                   DEC     HL          ;DECREMENT THE COUNT
    255  016B  22 00 00  E          LD      (SLEWCT),HL ;STORE NEW COUNT
    256  016E  7C                   LD      A,H         ;SET FLAGS FOR
    257  016F  B5                   OR      L           ; ANY/NONE LEFT
    258  0170  32 00 00  E          LD      (ADDROK),A  ;(SET "IX-1"-IS-OKAY)
    259  0173  C9                   RET                 ;(CALLER USES FLAGS)
    260
```

```
ERR LINE  ADDR  B1 B2 B3 B4           SLEW RATE/PEAK-TO-PEAK
    04-AUG-81 18:01 PAGE    5

261                                  ;**********************************
    262                                  ;* SUBROUTINE 'MARKIT' MARKS THE CURRENT  *
    263                                  ;* VALUE OF THE HL-PAIR AS A POINT-OF-    *
    264                                  ;* INTEREST (POSSIBLY AFTER FINDING A     *
    265                                  ;* SLIGHTLY-MORE INTERESTING POINT IN ITS *
    266                                  ;* NEIGHBORHOOD), SCORES THE SEGMENT      *
    267                                  ;* BASED ON ITS SLEW-RATE AND PEAK-TO-    *
    268                                  ;* PEAK VALUES, AND SAVES ITS SCORE AND   *
    269                                  ;* LOCATION IF THIS IS A NEW MAXIMUM.     *
    270                                  ;**********************************
    271
    272  0174  EB            MARKIT: EX      DE,HL        ;SAVE POTENTIAL "RIGHT"
    273  0175  2A 00 00    E         LD      HL,(XLEFT)   ;GET PREVIOUS"XRIGHT"
    274  0178                        OR      ;TURN CARRY-FLAG OFF
    275  0179  ED 52                 SBC     HL,DE        ;(NEW)TO RIGHT OF (OLD)?
    277  017B  C0                    RET     NC           ;NO: DON'T BOTHER
    278  017C  EB                    EX      DE,HL        ;YES:GET NEW(XRIGHT)BACK
    279  017D  22 00 00    E         LD      (XRIGHT),HL  ;STORE NEW "XRIGHT"
    280  0180  11 00 00    E         LD      DE,CSRAM     ;POINT TO START OF DATA
    281  0183  01 FA FF              LD      BC,-6        ;ARE WE WITHIN 6
    282  0186  09                    ADD     HL,BC        ; SAMPLES OF THE
    283  0187                        CLR                  ;   LEFT END OF
    285  0188  ED 52                 SBC     HL,DE        ;    THE ECM BUFFER?
    286  018A  38 58                 JR      C,MK35-$     ;YES: NO LOCAL SEARCH
    287  018C  3A 00 00    E         LD      A,(LASTYP)   ;NO: WAS LAST SLOPE
    288  018F                        TEST                 ;  "FLAT" ?
    290  0190  2A 00 00    E         LD      HL,(XRIGHT)  ;(POINT TO ORIGINAL)
    291  0193  28 1A                 JR      Z,MK25-$     ;YES: MK25
    292                              ;-------------------------------------
    293                              ; THIS POINT IS NOT NEAR THE EDGES OF THE
    294                              ; BUFFER, AND NOT ON THE RIGHT SIDE OF A
    295                              ; BASICALLY-FLAT SEGMENT.  SEARCH (WITHIN 6
    296                              ; DOTS) FOR A BETTER LOCAL MINIMUM/MAXIMUM.
    297                              ;-------------------------------------
    298  0195  4E                    LD      C,(HL)       ;GET ORIGINAL SAMPLE
    299  0196  11 FA FF              LD      DE,-6        ;START SEARCH AT SAMPLE
    300  0199  19                    ADD     HL,DE        ; 6 DOTS TO ITS LEFT
    301  019A  E6 80                 AND     10000000B    ;GET SIGN OF SLOPE
    302  019C  57                    LD      D,A          ;SAVE FOR COMPARISON
    303  019D  06 0D                 LD      B,13         ;6 ON LEFT+ORIG+6 ON RT
    304  019F  7E            MK10:   LD      A,(HL)       ;GET THIS SAMPLE VALUE
    305  01A0  91                    SUB     C            ;COMPARE TO ORIGINAL
    306  01A1  28 09                 JR      Z,MK20-$     ;SAME? YES: MK20
    307  01A3  E6 80                 AND     10000000B    ;NO: GET SIGN OF DIFF
    308  01A5  BA                    CP      D            ;SAME AS SEGMENT'S SIGN?
    309  01A6  20 04                 JR      NZ,MK20-$    ;NO: MK20
    310  01A8  4E                    LD      C,(HL)       ;YES: SAVE NEW MIN/MAX
    311  01A9  22 00 00    E         LD      (XRIGHT),HL  ; AND ITS LOCATION
    312  01AC  23            MK20:   INC     HL           ;POINT TO NEXT SAMPLE
    313  01AD  10 F0                 DJNZ    MK10-$       ;MORE TO CHECK? YES:MK10
    314                              ;-------------------------------------
    315                              ; SEARCH FOR FLAT SUB-SEGMENT OF 3 CONSECUTIVE
    316                              ; NEARLY-IDENTICAL SAMPLES (FLAT SPOT), TO THE
    317                              ; LEFT OR RIGHT OF THIS POINT (DEPENDING ON
    318                              ; "LASTYP").  IF THERE IS SUCH A SPOT, MOVE THE
    319                              ; POINTER TO THE LEFT OR RIGHT END OF THE SPOT.
    320                              ;-------------------------------------
    321  01AF  2A 00 00    E MK25:   LD      HL,(XRIGHT)  ;GET CURRENT POINTER
    322  01B2  01 FF 02              LD      BC,02FFH     ;COUNTER=2; "OTHER"=-1
    323  01B5  3A 00 00    E         LD      A,(LASTYP)   ;GET PREVIOUS SLOPE
    324  01B8                        TEST                 ;WAS IT ZERO?
    326  01B9  20 16                 JR      NZ,MK30-$    ;NO: MK30
    327  01BB  11 F8 FF              LD      DE,-8        ;YES: START CHECKING AT
    328  01BE  19                    ADD     HL,DE        ; 8 SAMPLES TO THE LEFT
    329  01BF  7E                    LD      A,(HL)       ;GET SAMPLE VALUE THERE
    330  01C0  23            MK26:   INC     HL           ;PT TO SAMPLE TO RIGHT
    331  01C1  CD 00 00    C         CALL    FLSPOT       ;"FLAT" HERE?
    332  01C4  20 15                 JR      NZ,MK35-$    ;NO: NOT A FLAT SPOT
    333  01C6  10 F8                 DJNZ    MK26-$       ;YES: 3 IN A ROW? NO: 26
    334  01C8  23            MK27:   INC     HL           ;PT TO SAMPLE TO RIGHT
    335  01C9  CD 00 00    C         CALL    FLSPOT       ;FLAT HERE, TOO?
    336  01CC  28 FA                 JR      Z,MK27-$     ;YES: MK27
    337  01CE  2B                    DEC     HL           ;PT TO END OF FLAT SPOT
```

```
ERR LINE  ADDR   B1 B2 B3 B4        SLEW RATE/PEAK-TO-PEAK
    04-AUG-81   18:01  PAGE   7

338  01CF   18 10                        JR     MK34-$    ;STORE THAT WITH MK34
    339  01D1   7E              MK30:        LD     A,(HL)    ;GET CURRENT-SAMPLE VALU
    340  01D2   2B              MK31:        DEC    HL        ;POINT TO SAMPLE TO LEFT
    341  01D3   CD 01 03    C                CALL   FLSPOT    ;"FLAT" HERE?
    342  01D6   20 0C                        JR     NZ,MK35-$ ;NO: NOT A FLAT SPOT
    343  01D8   10 F8                        DJNZ   MK31-$    ;YES: 3 IN A ROW? NO: 31
    344  01DA   2B              MK32:        DEC    HL        ;POINT TO SAMPLE TO LEFT
    345  01DB   CD 01 03    C                CALL   FLSPOT    ;FLAT HERE, TOO?
    346  01DE   28 FA                        JR     Z,MK32-$  ;YES: MK32
    347  01E0   23                           INC    HL        ;PT TO END OF FLAT SPOT
    348  01E1   22 00 00    E   MK34:        LD     (XRIGHT),HL ;STORE NEW POINTER
    349                                   ; ------------------------------
    350                                   ; DONE WITH ANY CHECKING FOR
    351                                   ; BETTER LOCAL MINIMUM/MAXIMUM
    352                                   ; ------------------------------
    353  01E4   ED 5B 00 00 E   MK35:        LD     DE,(XLEFT) ;POINT TO LEFT SIDE
    354  01E8   1A                           LD     A,(DE)    ;GET VALUE FROM THERE
    355  01E9   2A 00 00    E                LD     HL,(XRIGHT) ;POINT TO RIGHT SIDE
    356  01EC   96                           SUB    (HL)      ;GET (XLEFT) - (XRIGHT)
    357  01ED   30 02                        JR     NC,MK40-$ ;NEGATIVE? NO: MK40
    358  01EF   ED 44                        NEG              ;YES: TAKE ABSOLUTE VALU
    359  01F1   32 00 00    E   MK40:        LD     (PKPKX),A ;SAVE AS LOCAL PK-PK
    360  01F4                                TEST             ;BE SURE "CARRY" IS OFF
    362  01F5   ED 52                        SBC    HL,DE     ;#DOTS BETWEEN LEFT, RT
    363  01F7   22 00 00    E                LD     (DIFF),HL ;SAVE AS "DIFF"
    364  01FA   11 FA 00                     LD     DE,250    ;SCALE UP BY 250 SO THAT
    365  01FD   CD 00 00    E                CALL   MLTADE    ; SOME PRECISION IS KEPT
    366  0200   50                           LD     D,B       ;MOVE PRODUCT FROM
    367  0201   59                           LD     E,C       ; BC-PAIR TO DE-PAIR
    368  0202   2A 00 00    E                LD     HL,(DIFF) ;GET #SAMPLES BETWEEN
    369  0205   CD 00 00    E                CALL   DIVIDE    ;GET A REPRESENTATION OF
    370  0208   EB                           EX     DE,HL     ; SLEW RATE IN HL-PAIR
    371  0209   22 00 00    E                LD     (SLEWX),HL ;SAVE AS LOCAL SLEW
    372  020C   2A 00 00    E                LD     HL,(DIFF) ;#SAMPLES BETWN, AGAIN
    373  020F   11 F1 FF                     LD     DE,-15    ;ARE THEY LESS THAN
    374  0212   19                           ADD    HL,DE     ; 15 SAMPLES APART?
    375  0213   2A 00 00    E                LD     HL,(SLEWX) ;(GET LOCAL SLEW)
    376  0216   38 0B                        JR     C,MK50-$  ;NO: MK50
    377  0218   3A 00 00    E                LD     A,(PKPKX) ;YES: GET 16-BIT EQUIV
    378  021B   11 11 00                     LD     DE,17     ;SCORE IS 17*(PKPK),
    379  021E   CD 00 00    E                CALL   MLTADE    ; NOT 250*(PKPK)/(DIFF)
    380  0221   60                           LD     H,B       ;MOVE PRODUCT FROM
    381  0222   69                           LD     L,C       ; BC-PAIR TO HL-PAIR
    382  0223   22 00 00    E   MK50:        LD     (SCORE),HL ;SAVE SEGMENT SCORE
    383  0226   EB                           EX     DE,HL     ;SAVE IN DE-PAIR
    384  0227   2A 00 00    E                LD     HL,(MAX)  ;GET MAX-SCORE-SO-FAR
    385  022A                                                 ;TURN CARRY-FLAG OFF
    387  022B   ED 7B                        ...              ;IS THIS SCORE HIGHER?
    388  022D   38 0B                        ...              ;NO: MK80
    389  022F   21 00 00    E                LD     HL,XLEFT  ;MOVE (XLEFT) -> ATMAX
    390  0232   11 00 00    E                LD     DE,ATMAX  ; (SCORE) -> MAX
    391  0235   01 07 00                     LD     BC,7      ; (SLEWX) -> SLEW
    392  0238   ED B0                        LDIR             ; (PKPKX) -> PKPK
    393  023A   3A 00 00    E   MK80:        LD     A,(TYPE)  ;GET CURRENT SLOPE TYPE
    394  023D   32 00 00    E                LD     (LASTYP),A ;SAVE AS PREVIOUS TYP
    395  0240   C9                           RET
    396                               ; ******************************************
    397                               ; *                                         *
    398                               ; * SUBROUTINE 'LSQFT' DOES A LEAST-SQUARES-*
    399                               ; * FIT OF A LINE THROUGH THE 8-SAMPLE      *
    400                               ; * ROLLING BUFFER.  SEE PETE BERNTSON'S    *
    401                               ; * MEMO "790409-PKB/COMM" FOR DERIVATION OF*
    402                               ; * MUCH OF THIS TECHNIQUE.                 *
    403                               ; ******************************************
    404
    405  0241   3A 00 00    E   LSQFT:       LD     A,(ADDROK) ;GET "IX-1"-IS-OK FLG
    406  0244                                TEST             ;OKAY TO USE "IX-1" ?
    407  0245   28 43                        JR     Z,LS15-$  ;NO: LS15
    408  0247   DD 7E 00                     LD     A,(IX)    ;YES: GET CURRENT SAMPLE
    409  024A   DD 96 FF                     SUB    (IX-1)    ;GET DIFFERNCE FROM LAST
    410  024D   30 08                        JR     NC,LS03-$ ;NEW < OLD? NO: LS03
```

```
ERR LINE  ADDR   B1 B2 B3 B4              SLEW RATE/PEAK-TO-PEAK
     04-AUG-81  18:01  PAGE   8

412  034F   FE FD                     CP      -3         ;YES: DIFF IS 4 OR MORE?
     413  0351   30 37                     JR      NC,LS15-$  ;NO: NOT STEEPLY-NEG
     414  0353   3E FF                     LD      A,-1       ;YES: FORCE A NEGATIVE
     415  0355   18 06                     JR      LS05-$     ; SLOPE AT THE EXIT
     416  0357   FE 04            LS03:    CP      4          ;DIFF IS 4 OR MORE?
     417  0359   38 2F                     JR      C,LS15-$   ;NO: NOT STEEPLY-POSITV
     418  035B   3E 01                     LD      A,1        ;YES: FORCE POS-SLOPE
     419  035D   32 00 00   E     LS05:    LD      (TYPE),A   ;STORE THE FORCED SLOPE
     420  0360   47                        LD      B,A        ;SAVE TYPE IN B-REGISTER
     421  0361   DD 4E 00                  LD      C,(IX)     ;SAVE ORIGINAL SAMPLE
     422  0364   CD 65 01   C     LS07:    CALL    NEXT       ;POINT TO NEXT SAMPLE
     423  0367   20 10                     JR      NZ,LS11-$  ;ANY LEFT? YES: LS11
     424  0369   3C                        INC     A          ;NO: (A=0) => A=1 NOW
     425  036A   32 00 00   E              LD      (SLEWCT),A ;COUNT = 1 LEFT
     426  036D   DD 2B            LS09:    DEC     IX         ;POINT TO LAST SAMPLE
     427  036F   DD 7E 00                  LD      A,(IX)     ;GET THAT SAMPLE VALUE
     428  0372   CD 31 01   C              CALL    LSQNIT     ;INITIALIZE TO THAT
     429  0375   3A 00 00   E              LD      A,(TYPE)   ;GET SLOPE-TYPE BACK
     430  0378   C9                        RET                ;RETURN WITH IT IN A-REG
     431  0379   79               LS11:    LD      A,C        ;GET ORIGINAL SAMPLE
     432  037A   DD 96 00                  SUB     (IX)       ;SUBTRAC TNEW SAMPLE VAL
     433  037D   28 EE                     JR      Z,LS09-$   ;SAME? YES: LS09
     434  037F   78                        LD      A,B        ;(GET SLOPE-TYPE IN A)
     435  0380   38 03                     JR      C,LS12-$   ;NO: ORIG<NEW? YES:LS12
     436  0382   3C                        INC     A          ;NO: SLOPE-TYPE = -1?
     437  0383   18 01                     JR      LS13-$     ;(HANDLE DECISION@LS13)
     438  0385   3D               LS12:    DEC     A          ;SLOPE-TYPE = +1?
     439  0386   28 DC            LS13:    JR      Z,LS07-$   ;SLOPE-TYPS SAME?YES:07
     440  0388   18 E3                     JR      LS09-$     ;NO,END OF SEGMENT: LS09
     441
     442                                   ;---- START OF LEAST-SQUARES-FIT ALGORITHM
     443
     444  038A   DD 7E 00         LSLF:    LD      A,(IX)     ;GET THIS SAMPLE
     445  038D   47                        LD      B,A        ;SAVE IN B-REGISTER
     446  038E   21 00 00   E              LD      HL,BUFFER  ;PT TO CIRCULR-BFR PTR
     447  0391   16 00                     LD      D,0        ;CREATE 16-BIT OFFSET
     448  0393   5E                        LD      E,(HL)     ; IN DE-PAIR
     449  0394   35                        DEC     (HL)       ;ADJUST POINTER
     450  0395   20 02                     JR      NZ,LS20-$  ;NOW ZERO? NO: LS20
     451  0397   36 08                     LD      (HL),8     ;YES: RESET POINTER
     452  0399   19               LS20:    ADD     HL,DE      ;POINT TO CURRENT SLOT
     453  029A   4E                        LD      C,(HL)     ;OLDEST VALUE TO C-REG
     454  029B   77                        LD      (HL),A     ;REPLACE WITH NEWEST VAL
     455  029C   69                        LD      L,C        ;MAKE 16-BIT EQUIVALENT
     456  029D   26 00                     LD      H,0        ; OF OLDEST VALUE
     457  029F   CD 30 00   E              CALL    NEGHL      ;GET 2'S COMPLEMENT
     458  02A2   22 00 00   E              LD      (NYOLD),HL ;STORE -(OLD)[16BITS]
     459  02A5   29                        ADD     HL,HL      ; * 2
     460  02A6   29                        ADD     HL,HL      ; * 4
     461  02A7   29                        ADD     HL,HL      ; * 8
     462  02A8   EB                        EX      DE,HL      ;DE <- 8 * (OLDEST)
     463  02A9   2A 00 00   E              LD      HL,(AN)    ;HL <- (AN)
     464  02AC   19                        ADD     HL,DE      ;HL <- (AN)-8*(OLDEST)
     465  02AD   CD 00 00   E              CALL    NEGHL      ;HL <- -(AN)+8*(OLDEST)
     466  02B0   EB                        EX      DE,HL      ;DE <- -(AN)+8*(OLDEST)
     467  02B1   2A 00 00   E              LD      HL,(BN)    ;HL <- (BN)
     468  02B4   19                        ADD     HL,DE      ;HL <- (BN)-(AN)+8*(OLD)
     469  02B5   22 00 00   E              LD      (BN),HL    ;NEW (BN)
     470  02B8   2A 00 00   E              LD      HL,(NYOLD) ;HL <- -(OLDEST)
     471  02BB   EB                        EX      DE,HL      ;DE <- -(OLDEST)
     472  02BC   2A 00 00   E              LD      HL,(AN)    ;HL <- (AN)
     473  02BF   19                        ADD     HL,DE      ;HL <- (AN)-(OLDEST)
     474  02C0   58                        LD      E,B        ;E <- (NEWEST)
     475  02C1   16 00                     LD      D,0        ;DE <- (NEWEST) [16BITS]
     476  02C3   19                        ADD     HL,DE      ;HL <- (AN)-(OLD)+(NEW)
     477  02C4   22 00 00   E              LD      (AN),HL    ;NEW (AN)
     478  02C7   54                        LD      D,H
     479  02C8   5D                        LD      E,L        ;DE <- (HL)
     480  02C9   29                        ADD     HL,HL      ; * 2
     481  02CA   19                        ADD     HL,DE      ; * 3
     482  02CB   29                        ADD     HL,HL      ; * 6
     483  02CC   19                        ADD     HL,DE      ; * 7
```

```
ERR LINE  ADDR   B1 B2 B3 B4         SLEW RATE/PEAK-TO-PEAK
    04-AUG-81  18:01  PAGE    9

484  02CD  29                    ADD    HL,HL    ; *14
    485  02CE  29                    ADD    HL,HL    ; 428
    486  02CF  EB                    EX     DE,HL    ;DE <- 28*(AN)
    487  02D0  2A 00 00         E    LD     HL,(BN)  ;HL <- (BN)
    488  02D3  29                    ADD    HL,HL    ;HL <- 2*(BN)
    489  02D4  29                    ADD    HL,HL    ;HL <- 4*(BN)
    490  02D5  29                    ADD    HL,HL    ;HL <- 8*(BN)
    491  02D6  19                    ADD    HL,DE    ;HL <- 8*(BN)+28*(AN)
    492  02D7  EB                    EX     DE,HL    ;CURRENT VALUE TO DE
    493  02D8  2A 00 00         E    LD     HL,(OFFSET) ;GET BIAS AMOUNT
    494  02DB  19                    ADD    HL,DE    ;REMOVE BIAS FROM VALUE
    495                               ;-----------------------------------
    496                               ; RETURN THE SEGMENT'S SLOPE-TYPE, BASED
    497                               ;  ON RESULTS OF THE LEAST-SQUARES-FIT.
    498                               ;    TYPE:  -1  (NEGATIVE SLOPE)
    499                               ;            0  (BASICALLY-FLAT = WITHIN
    500                               ;                NOISE LIMIT)
    501                               ;           +1  (POSITIVE SLOPE)
    502                               ;-----------------------------------
    503  02DC  7C                    LD     A,H      ;GET HI BYTE OF SLOPE
    504  02DD                         TEST            ;HI BYTE IS ZERO?
    506  02DE  20 09                 JR     NZ,LS30-$ ;NO: LS30
    507  02E0  3E 1D                 LD     A,29     ;YES: GET NOISE T'HOLD
    508  02E2  BD                    CP     L        ;ABOVE NOISE THRESHOLD?
    509  02E3  30 17                 JR     NC,LS50-$ ;NO: LS50
    510  02E5  3E 01         LS27:   LD     A,1      ;YES: SIGN IS " + "
    511  02E7  18 14                 JR     LS60-$
    512  02E9  F2 E5 02     C LS30:  JP     P,LS27   ;POSITIVE? YES: LS27
    513  02EC  CD 00 00     E        CALL   NEGHL    ;GET ABS.VALUE OF SLOPE
    514  02EF  7C                    LD     A,H      ;NOW GET HI BYTE AGAIN
    515  02F0                         TEST            ;IS IT ZERO?
    517  02F1  20 05                 JR     NZ,LS40-$ ;NO: LS40
    518  02F3  3E 1D                 LD     A,29     ;YES: GET NOISE T'HOLD
    519  02F5  BD                    CP     L        ;ABOVE NOISE THRESHOLD?
    520  02F6  30 04                 JR     NC,LS50-$ ;NO: LS50
    521  02F8  3E FF         LS40:   LD     A,-1     ;SIGN IS " - "
    522  02FA  18 01                 JR     LS60-$
    523  02FC                 LS50:  CLR             ;SIGN IS " 0 "
    525  02FD  32 00 00     E LS60:  LD     (TYPE),A ;SAVE AS SLOPE TYPE
    526  0300  C9                    RET
    527
    528                               ;**********************************
    529                               ;* SUBROUTINE 'FLSPOT' CHECKS TO SEE IF THIS *
    530                               ;* IS A BASICALLY-FLAT SPOT: SAME VALUE AS   *
    531                               ;* BEFORE, OR THE SAME AS ONE OTHER VALUE    *
    532                               ;* THAT DIFFERS BY ONLY PLUS-OR-MINUS-ONE    *
    533                               ;* FROM THE ORIGINAL VALUE.                  *
    534                               ;**********************************
    535
    536  0301  BE            FLSPOT: CP     (HL)     ;IS IT JUST-PLAIN FLAT?
    537  0302  C8                    RET    Z        ;YES: THAT WAS EASY
    538  0303  57                    LD     D,A      ;NO: SAVE IN D-REGISTER
    539  0304  79                    LD     A,C      ;IS THIS THE FIRST OTHER
    540  0305  FE FF                 CP     -1       ;  VALUE BEING CONSIDRD?
    541  0307  28 03                 JR     Z,FS10-$ ;YES: FS10
    542  0309  BE                    CP     (HL)     ;NO: THIS VS. "OTHER"
    543  030A  7A                    LD     A,D      ;(GET ORIGINAL BACK)
    544  030B  C9                    RET             ;RETURN WITH THAT TEST
    545  030C  3C            FS10:   INC    A        ;MIGHT BE "FLAT"+1
    546  030D  BE                    CP     (HL)     ;WAS IT THAT?
    547  030E  28 03                 JR     Z,FS20-$ ;YES: FS20
    548  0310  3D                    DEC    A        ;NO: MIGHT
    549  0311  3D                    DEC    A        ;  BE "FLAT"-1
    550  0312  BE                    CP     (HL)     ;RETURN WITH THAT TEST
    551  0313  7A                    LD     A,D
    552  0314  C9                    RET
    553  0315                FS20:   LD     C,A      ;SAVE OTHER VALUE
    554  0315  79                    LD     A,D      ;GET ORIGINAL BACK
    555  0316  7A
    556  0317  C9                    RET

ASSEMBLER ERRORS =     0
```

SYMBOL TABLE

| Symbol | Type | Addr | Symbol | Type | Addr | Symbol | Type | Addr | Symbol | Type | Addr |
|---|---|---|---|---|---|---|---|---|---|---|---|
| ADDROK | E | 0001 | AN | E | 0000 | ATMAX | E | 0002 | AV | E | 0003 |
| BN | E | 0004 | BUFFER | E | 0005 | CSRAM | E | 0006 | DIFF | E | 0007 |
| DIVIDE | E | 0008 | EGMCOL | E | 0009 | EGMSCL | E | 000A | EGMSIZ | E | 000B |
| ERROR | E | 000C | FLSPOT | C | 0301 | FS10 | C | 030C | FS20 | C | 0313 |
| LASTYP | E | 000D | LN10 | C | 0138 | LS03 | C | 0257 | LS05 | C | 025D |
| LS07 | C | 0264 | LS09 | C | 026D | LS11 | C | 0279 | LS12 | C | 0285 |
| LS13 | C | 0286 | LS15 | C | 023A | LS20 | C | 0293 | LS27 | C | 02E5 |
| LS30 | C | 02E9 | LS40 | C | 02F8 | LS50 | C | 02FC | LS60 | C | 02FD |
| LSQFT | C | 0241 | LSQNIT | C | 0131 | MARKIT | C | 0174 | MAX | E | 000E |
| MEAS | E | 000F | MEMORY | M | 0000 | MK10 | C | 019F | MK20 | C | 01AC |
| MK25 | C | 01AF | MK26 | C | 01C0 | MK27 | C | 01C8 | MK30 | C | 01D1 |
| MK31 | C | 01D2 | MK32 | C | 01DA | MK34 | C | 01E1 | MK35 | C | 01E4 |
| MK40 | C | 01F1 | MK50 | C | 0223 | MK60 | C | 023A | MLTADE | E | 0010 |
| MLTPLY | E | 0011 | NARG | | 0033 | NICHL | E | 0012 | NEXT | C | 0165 |
| NOISE | E | 0013 | NYQLD | E | 0014 | OFFSET | E | 0015 | PKPK | E | 0016 |
| PKPKX | E | 0017 | RESULT | E | 0013 | SCOPE | E | 0019 | SHIFT | C | 015B |
| SL10 | C | 0330 | SL20 | C | 0143 | SL30 | C | 0150 | SL35 | C | 006F |
| SL40 | C | 0173 | SLF1 | C | 0091 | SL55 | C | 00A0 | SL60 | C | 00BB |
| SL65 | C | 0103 | SL70 | C | 0010 | SL75 | C | 00F3 | SL30 | C | 0104 |
| SL90 | C | 0114 | SLF5 | C | 0117 | SL97 | C | 011F | SL92 | C | 0122 |
| SL99 | C | 0120 | SLF4 | C | 0019 | SLFCT | E | 001D | SLEWPT | D | 0000 |
| SLEWRT | C | 0092 | SLFX | C | 011C | SLPWPK | C | 0000 | STACK | S | 0000 |
| STRING | E | 0011 | TYPE | C | 0015 | VLEFT | E | 001F | XRIGHT | E | 0020 |

I claim:

1. An evaluation system for use in conjunction with a body implantable body stimulator, the body stimulator including a stimulaton delivering and depolarization sensing lead system, said evaluation system comprising:
    input means adapted for connection to said lead system;
    means for digitizing depolarization signals sensed by said lead system;
    computing means including means for identifying excursions in the digitized depolarization signals and means for evaluating identified excursions in accordance with a preselected plurality of merit criteria; and
    output means for giving an indication of at least that excursion having the highest merit that satisfies said merit criteria.

2. The system of claim 1 wherein said output means gives an indication of the first evaluated excursion satisfying said merit criteria and excursions evaluated subsequent to said first indicated excursion having greater merit than the last indicated excursion.

3. The system of claim 2 wherein said output means comprises means for displaying peak-to-peak amplitude of indicated excursions.

4. The system of claim 3 wherein said displaying means comprises digital displaying means.

5. The system of claim 1 wherein said merit criteria include excursion slew rate and excursion peak-to-peak amplitude.

6. The system of claim 5 wherein said merit criteria further include excursion duration.

7. The system of claim 6 wherein said output means gives an indication of the first evaluated excursion satisfying said merit criteria and excursions evaluated subsequent to said first indicated excursion having greater merit than the last indicated excursion.

8. The system of claim 6 wherein said merit criteria further include, for excursions subsequent to a first indicated excursion, occurrence within a preselected interval after said first indicated excursion and the relative peak-to-peak amplitude relative to the last indicated excursion within said preselected interval.

9. The system of claim 8 wherein said output means comprises means for displaying peak-to-peak amplitude of indicated excursions.

10. The system of claim 9 wherein said displaying means comprises digital displaying means.

11. The system of claim 10 wherein said excursion identifying means identifies excursions having a negative slope.

12. The system of claim 11 wherein said merit criteria comprise an excursion slew rate greater than 0.1 V/sec., an excursion peak-to-peak amplitude greater than 1.0 mV, and an excursion duration greater than 3 msec. but no greater than 30 msec.

13. The system of claim 12 wherein said preselected interval is 200 msec.

14. The system of claim 13 wherein said output means gives an indication of the first evaluted excursion satisfying said merit criteria and excursions evaluated subsequent to said first indicated excursion during said preselected interval that satisfy said merit criteria and have a peak-to-peak amplitude greater than the last indicated excursion during said preselected interval.

15. The system of claim 1 wherein said excursion identifying means identifies excursions having a negative slope.

* * * * *